(12) United States Patent
Vagos et al.

(10) Patent No.: US 8,427,645 B2
(45) Date of Patent: Apr. 23, 2013

(54) MUELLER MATRIX SPECTROSCOPY USING CHIROPTIC

(75) Inventors: Pedro Vagos, Chennevieres (FR); Pablo I. Rovira, Palo Alto, CA (US)

(73) Assignee: Nanometrics Incorporated, Milpitas, CA (US)

( * ) Notice: Subject to any disclaimer, the term of this patent is extended or adjusted under 35 U.S.C. 154(b) by 296 days.

(21) Appl. No.: 12/987,530

(22) Filed: Jan. 10, 2011

(65) Prior Publication Data

US 2012/0176618 A1 Jul. 12, 2012

(51) Int. Cl.
G01J 4/00 (2006.01)
(52) U.S. Cl.
USPC .......................................................... 356/369
(58) Field of Classification Search .................. 356/369; 250/559.09
See application file for complete search history.

(56) References Cited

U.S. PATENT DOCUMENTS

| | | | |
|---|---|---|---|
| 5,045,701 A | 9/1991 | Goldstein et al. | |
| 5,956,147 A * | 9/1999 | Jellison et al. | 356/369 |
| 7,115,858 B1 | 10/2006 | Holden et al. | |
| 7,301,633 B2 * | 11/2007 | Gibbs et al. | 356/369 |
| 2005/0094144 A1 * | 5/2005 | Gibbs et al. | 356/365 |
| 2007/0263219 A1 | 11/2007 | De Martino et al. | |
| 2011/0080585 A1 | 4/2011 | Rabello et al. | |

FOREIGN PATENT DOCUMENTS

WO WO 2010/049652 A1 5/2010

OTHER PUBLICATIONS

International Search Report andWritten Opinion mailed on May 3, 2012 for PCT Application No. PCT/US2011/066535 filed on Dec. 21, 2011, 17 pages.
Ferrieu, F. et al. (Dec. 21, 2010). "Analysis of textured films and periodic grating structures with Mueller matrices: A new challenge in instrumentation with the generation of angle-resolved SE polarimeters," *Thin Solid Films*, vol. 519(2011):2608-2612.
Li, J. et al. (Jan. 1, 2009). "Scatterometry measurement of asymmetric gratings," *Proceedings of SPIE*, vol. 7520: 75201B-75201B-10.
Li, J. et al. (Jan. 1, 2010). "Advanced diffraction-based overlay for double patterning," *Proceedings of SPIE*, vol. 7638: 7638C-7638C-10.
Li, J. et al. (Oct.-Dec. 2010). "Mueller matrix measurement of asymmetric gratings," *Journal of Micro/Nanolithography, MEMS and MOEMS*, vol. 9(4): 041305-1-041305-8.
Nerbø, S. et al. (Jul. 7, 2010). "Characterization of inclined GaSb nanopillars by Mueller matrix ellipsometry," *Journal of Applied Physics*, vol. 108:014307-1-14307-8.

* cited by examiner

*Primary Examiner* — Roy M Punnoose
(74) *Attorney, Agent, or Firm* — Silicon Valley Patent Group LLP

(57) ABSTRACT

An optical metrology device produces a broadband beam of light that is incident on and reflected by a sample and introduces multiple variations in the polarization state of the beam of light induced by an optical chiral element. Using the detected light, the Muller matrix or partial Mueller matrix for the sample is determined, which is then used to determine a characteristic of the sample. For example, simulated spectra for a Mueller matrix for a model is fit to the measured spectra for the Mueller matrix of the sample by adjusting the parameters of the model until an acceptable fit between the simulated spectra and measured spectra from the Mueller matrices is produced. The varied parameters are then used as the sample parameters of interested, which can be reported, such as by storing in memory or displaying.

15 Claims, 9 Drawing Sheets

MUELLER MATRIX SPECTROSCOPY USING CHIROPTIC

BACKGROUND

The semiconductor industry, as well as other complex nanotechnology process industries, requires very tight tolerances in process control. As dimensions of chip continue to shrink, the tolerance requirements continue to become tighter. Accordingly, new more precise ways of measuring very small dimensions, e.g., on the order of a few nanometers, is desired. At this scale, typical microscopies, such as optical microscopy, or Scanning Electron Microscopy, are not suitable to obtain the desired precision, or to make quick, non-invasive measurements, which are also desirable.

Optical spectroscopic techniques have been presented as a solution. The basic principle of optical spectroscopic techniques is to reflect broadband light from the target, and measure the reflected spectrum. The received signal can be based simply on the reflectance of the light from the sample, or the change in polarization state (Psi, Del) of the light caused by the sample. The spectrum is then modeled to retrieve the geometries or other desired parameters of the illuminated sample.

Applications, commonly classed as "model-based applications", consist of inferring a certain number of parameters of interest (e.g., thicknesses, critical dimension (CD), side wall angle (SWA), etc) that describes the sample (or "target"). The sample may be measured using Ellipsometry, Reflectometry or other techniques and a theoretical model is used to simulate the spectrum. The model is generated based on several parameters that described the target. Some of these parameters, if not all, are the parameters of interest. Using the described model, a simulated spectrum may be mathematically generated. By fitting the simulated spectrum to the experimental spectrum by adjusting the model parameters, the real value of these parameters can be inferred.

SUMMARY

An optical metrology device produces a broadband beam of light that is incident on and reflected by a sample and introduces multiple variations in the polarization state of the beam of light induced by an optical chiral element. Using the detected light, the Mueller matrix or partial Mueller matrix for the sample is determined, which is then used to determine a characteristic of the sample. For example, simulated spectra for a Mueller matrix for a model is fit to the measured spectra for the Mueller matrix of the sample by adjusting the parameters of the model until an acceptable fit between the simulated spectra and measured spectra from the Mueller matrices is produced. The varied parameters are then used as the sample parameters of interested, which can be reported, such as by storing in memory or displaying.

DETAILED DESCRIPTION

Figure 1:
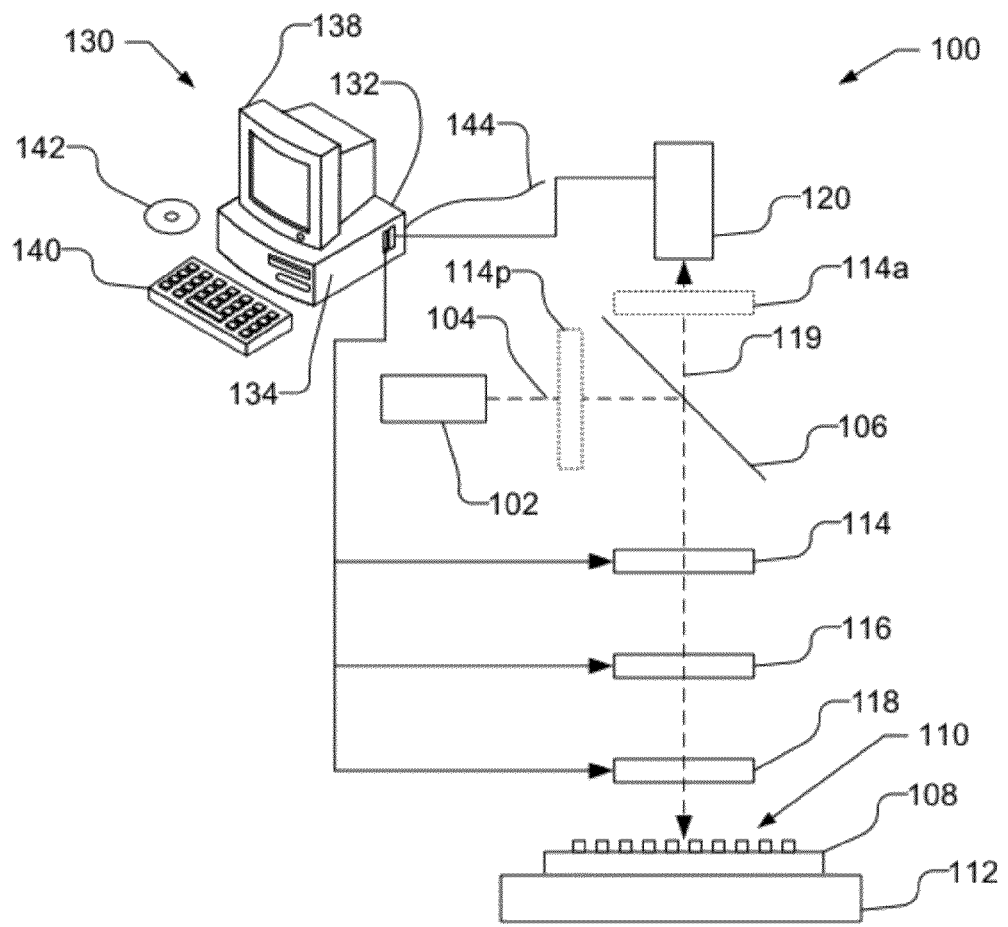
FIG. 1 illustrates a normal incidence metrology device with a chiroptic and that may be used to measure spectra a for full or part of a sample Muller matrix to determine a characteristic of a sample.

FIG. 1 illustrates a normal incidence metrology device 100 that may be used to measure a sample Muller matrix spectra or at least parts of the sample Muller matrix, where parts indicates a subset of the 16 elements that compose the Mueller matrix or a set of M independent linear combinations of some of the 16 elements of the Mueller matrix, M being less or equal to 16. With parts of or the full sample Muller matrix, the spectra may be used, e.g., in "model-based applications" to determine the constituents of the sample and therefore the parameters of interest of the sample.

Metrology device 100 includes a broad-band light source 102 that produces a beam of light 104. A beam splitter 106 directs the beam of light 104 towards a sample 108, which is illustrated as including a grating pattern 110. The sample 108 is held and positioned on a stage 112. The beam of light 104 passes through a polarizer 114, a retarder 116, and a chiroptic 118, sometimes referred to as a chiroptical element, before being incident on the sample 108. The reflected light 119 passes back through the chiroptic 118, retarder 116, and polarizer 114 before being directed by the beam splitter 106 to a spectrometer 120. Of course, additional optical components, such as lenses and field stops may be included within the metrology device. Further, if desired, one or more of the optical components may be positioned in different positions along the beam path or removed. For example, if desired, the polarizer 114 may be replaced with a polarizer 114p between the light source 102 and the beam splitter 106 and an analyzer 114a between the beam splitter 106 and the spectrometer 120. Moreover, if desired, the retarder 116 may be removed, particularly if a rotating polarizer 114 is used.

The state of polarization of the beam of light 104 undergoes a succession of changes when it passes through the different optical media in the metrology device 100. The beam of light 104 is initially randomly polarized at the source level 102, it becomes linear polarized at azimuth "p" in its first pass in the polarizer 114, suffers a phase retardation "d" at the retarder 116 to become elliptically polarized, and the chiroptic 118 rotate the electromagnetic field by an angle "t". Phase retardation "d" indicates a phase shift of "d" in degrees between the electrical field projections at the fast and slow axis of the retarder 116. A new change of the state of polarization and intensity is introduced to the beam of light 104 when it reflects from the sample 108 to become the reflected beam of light 119. The reflected beam 119 is then affected successively by a rotation "t" by the chiroptic 118, a phase retardation "d" by the retarder 116, and finally only the polarization component along the azimuth 'p" passes through the polarizer 114 to enter the spectrometer 120.

The spectrometer 120 as well as the polarizer 114, retarder 116, and chiroptic 118 are coupled to a computer 130, which includes a processor 132 with memory 134, as well as a user interface including e.g., a display 138 and input devices 140. A computer-usable medium 142 having computer-readable program code embodied may be used by the computer 130 for causing the processor to control the metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 142, which may be any device or medium that can store code and/or data for use by a computer system such as processor 132. The computer-usable medium 142 may be, but is not limited to, magnetic and optical storage devices such as disk drives, magnetic tape, compact discs, and DVDs (digital versatile discs or digital video discs). A communication port 144 may also be used to receive instructions that are used to program the computer 130 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 2:
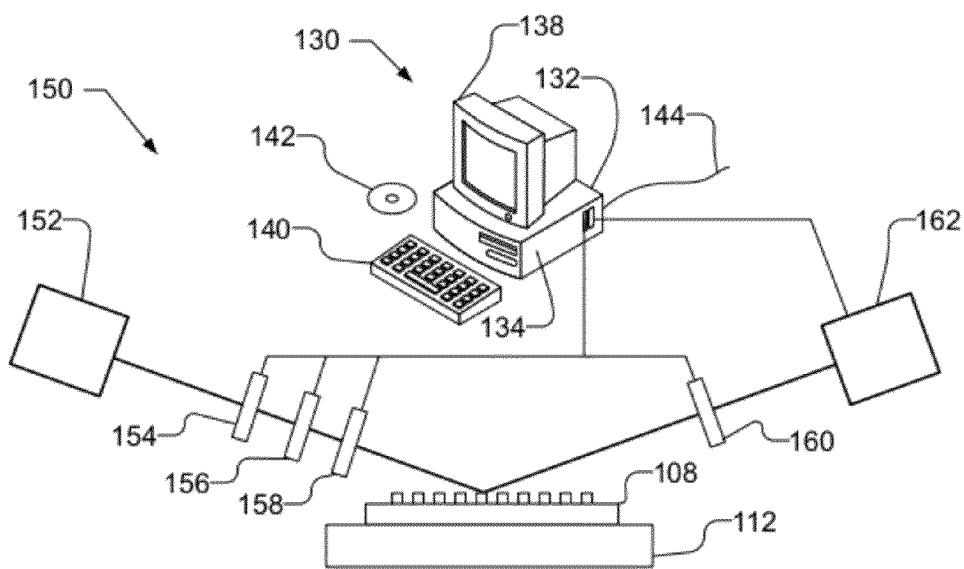
FIG. 2 illustrates an oblique incidence metrology device with a chiroptic and that may be used to measure spectra for a full or part of a sample Muller matrix to determine a characteristic of a sample.
Figure 3:
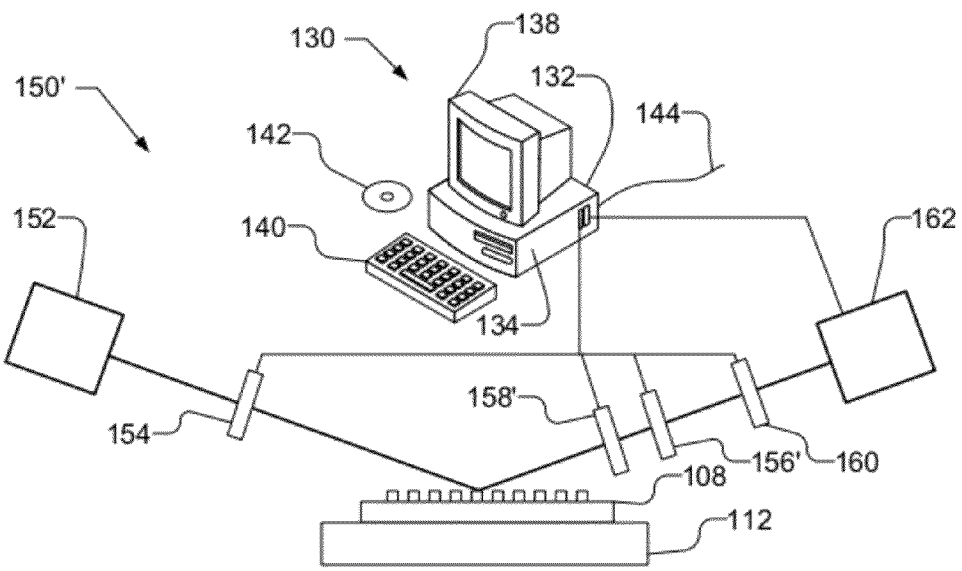
FIG. 3 illustrates another oblique incidence metrology device with a chiroptic and that may be used to measure spectra for a full or part of a sample Muller matrix to determine a characteristic of a sample.

If desired, an oblique incidence metrology device 150 may be used to measure a full or part of a sample Muller matrix spectra, as illustrated in FIG. 2. The metrology device 150 is, for example, has a spectroscopic ellipsometer configuration with a light source 152, polarizer 154, retarder 156, and chiroptic 158 disposed before the sample 108, and an analyzer 160 and detector 162 disposed after the sample 108. As with metrology device 100, shown in FIG. 1, a computer 130 is connected to the detector 162, as well as the polarizer 154, retarder 156, chiroptic 158, and the analyzer 160. FIG. 3 illustrates a metrology device 150' that is similar to the metrology device 150 shown in FIG. 2, but with the retarder 156' and chiroptic 158' disposed after the sample 108.

As an introduction to the notation used herein, (X,Y) defines the plane upon which the sample 108 lies, i.e., the directions of the X and Y axes define the orientation of the sample. The Mueller matrix for the sample is defined according these directions. All the azimuths of the polarizer and retarder axis are referenced to X. Other commonly used notations used herein are provided in Table 1 below.

TABLE 1

| NOTATION | MEANING |
|---|---|
| p | polarizer axis azimuth |
| c | retarder fast axis azimuth |
| d | retardation between fast and slow axis introduced by the retarder |
| t | rotation of the electromagnetic field by the chiroptics |
| M | sample Mueller matrix |
| $I_{in}$ | source optical intensity |

TABLE 1-continued

| NOTATION | MEANING |
|---|---|
| $I_{out}$ | optical intensity at the spectrometer entry. |

The above described quantities, except "p", are typically functions of the wavelength $\lambda$. The optical intensity at the entry of the spectrometer 120 can be expressed as:

$$I_{out}(M,p,c,d,t) = I_{in} T(M,p,c,d,t) \quad \text{eq. 1}$$

where T(M,p,c,d,t) is the transmittance of the system at a given wavelength $\lambda$ and for a given sample M, polarizer azimuth p, retarder azimuth c and phase d, and chirality "t". The system transmittance T may be written as:

$$T = U_0 + U_1 \cdot \cos(2c) + U_2 \cdot \sin(2c) + U_3 \cdot \cos(4c) + U_4 \cdot \sin(4c) + U_5 \cdot \cos(6c) + U_6 \cdot \sin(6c) + U_7 \cdot \cos(8c) + U_8 \cdot \sin(8c) \quad \text{eq. 2}$$

where $U_h$ are the Fourier coefficients of T for the retarder azimuth angle "c" and are functions of M, p, d and t. A more generic form for T can be written as:

$$T = \sum_{h=1}^{9} \sum_{i=1}^{5} \sum_{j=1}^{5} \sum_{g=1}^{5} \sum_{k=1}^{16} U_{hijgk} \cdot M_k \cdot \Theta_g \cdot \Phi_j \cdot \Lambda_i \cdot \Omega_h \quad \text{eq. 3}$$

with $[\Omega_h] = [1 \cos(2c) \sin(2c) \cos(4c) \sin(4c) \cos(6c) \sin(6c) \cos(8c) \sin(8c)]$ $[\Lambda_i] = [1 \cos(2p) \sin(2p) \cos(4p) \sin(4p)]$ $[\Phi_j] = [1 \cos(2t) \sin(2t) \cos(4t) \sin(4t)]$ $[\Theta_g] = [1 \cos(d) \sin(d) \cos(2d) \sin(2d)]$ $[M_k] = \text{vector}(M)$ $= [M_{11} M_{12} M_{13} M_{14} M_{21}$
$M_{22} M_{23} M_{24} M_{31} M_{32} M_{33} M_{34} M_{41} M_{42} M_{43} M_{44}]$ The coefficients $U_{hijgk}$ are constants and do not depend on the wavelength $\lambda$ nor do they depend on any of the quantities M, p, c, d and t. The coefficients $U_{hijgk}$ depend only on the sequence of the optical media that interacts with the light beam. These constants can easily be found by developing T in the frame of the Stokes formalism as a product of the Mueller matrices for each optical element:

$$T = [1000] \cdot MP^{back} \cdot MC^{back} \cdot MR^{back} \cdot M \cdot MR^{forward} \cdot MC^{forward} \cdot MP^{forward} \cdot [1000]^T \quad \text{eq. 4}$$

where $MP^x$ are the polarizer matrices, $MC^x$ the retarder matrices, $MR^x$ the rotation matrices for the chiroptic and M the sample Mueller matrix and the index "x" stands for the forward and backward beam. The coefficients $U_{hijgk}$ represent a sparse tensor with 9×5×5×5×16=18000 elements where most of these elements are zeros, only 275 elements are non-zero.

In the stokes formalism the interaction of a beam of light with a given media (e.g. optical device, reflection on a sample, etc. . . . ) is described by the means of a Mueller matrix of that media (a 4×4 matrix) and the Stokes vector of the beam of light (a 4×1 vector):

$$\begin{pmatrix} S_0 \\ S_1 \\ S_2 \\ S_3 \end{pmatrix}^{out} = \begin{pmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{pmatrix} \begin{pmatrix} S_0 \\ S_1 \\ S_2 \\ S_3 \end{pmatrix}^{in} \quad \text{eq. 5}$$

Both Mueller matrix and Stokes vector contain only real elements. The Stokes vector is defined as:

$$S = \begin{pmatrix} S_0 \\ S_1 \\ S_2 \\ S_3 \end{pmatrix} = \begin{pmatrix} P_{0°} + P_{90°} \\ P_{0°} - P_{90°} \\ P_{45°} - P_{-45°} \\ P_{RHC} - P_{LHC} \end{pmatrix}. \quad \text{eq. 6}$$

where $P_0°$, $P_{90}°$, $P_{45}°$, $P_{-45}°$ are respectively the beam power of the components of the electric field at 0°, 90°, 45° and −45° degrees azimuth, while $P_{RHC}$ and $P_{LHC}$ are the power of the components of the electric field "right hand circular" polarized and "left hand circular" polarized. The first element $P_0°+P_{90}°$ represent the total power of the beam. The Mueller matrix and Stokes formalism are well known to those of ordinary skill in the art and are generally described, e.g., in "Polarized Light, second edition revised and expanded", D. Goldstein, CRC Press, 2 edition (Jun. 13, 2003), which is incorporated herein by reference.

The formula given in equation 3 is very practical from a computational point of view since it allows to quickly calculate the response of the system for a given configuration set by the values of p, c, d, t and M. From equations 1 and 3 we can express the optical intensity at the entry of the spectrometer as:

$$I_{out} = I_{in} \sum_{k=1}^{16} \left[ \sum_{h=1}^{9} \sum_{i=1}^{5} \sum_{j=1}^{5} \sum_{g=1}^{5} U_{hijgk} \cdot \Theta_g \cdot \Phi_j \cdot \Lambda_i \cdot \Omega_h \right] \cdot M_k \quad \text{eq. 7}$$

$$I_{out} = I_{in} \sum_{k=1}^{16} A_k(p, c, d, t) \cdot M_k$$

The metrology system coefficient $A_k$ is a function of the optics in the metrology system and includes a set of 16 constants (k=1, 2, ... 16) for each configuration (p,c,d,t), which may be calculated using the formulas of Table 2, below, which shows the full expressions for the coefficients $A_k$ as functions of p,c,d and t. For readability reasons all cosines and sines are noted by the capitals "C" and "S" followed by its arguments in lower case, for example cos(6c)=C6c and sin(d)=Sd.

TABLE 2

| | |
|---|---|
| $A_1 =$ | ¼ |
| $A_2 =$ | [(C2p · C2t − S2p · S2t)(Cd + 1) − C4c(C2p · C2t − S2p · S2t)(Cd − 1) − S4c(C2p · S2t − S2p · C2t)(Cd − 1)](1/8) |
| $A_3 =$ | [(C2p · S2t + S2p · C2t)(Cd + 1) − C4c(C2p · S2t − S2p · C2t)(Cd − 1) + S4c(C2p · C2t − S2p · S2t)(Cd − 1)](⅛) |
| $A_4 =$ | [C2c · S2p + S2c · C2p] · Sd(¼) |
| $A_5 =$ | [(C2p · S2t − S2p · C2t)(Cd + 1) − C4c(C2p · C2t − S2p · S2t)(Cd − 1) + S4c(C2p · S2t + S2p · C2t)(Cd − 1)](⅛) |
| $A_6 =$ | {[(3 + 4 · Cd + C2d) + C4t(3 − 4 · Cd + C2d) + (C4p · C4t − S4p · S4t)(3 + 4 · Cd + C2d)] + C4c[−(C4t + 1) − C4p(C4t + 1) + S4p · S4t](C2d − 1) + |

TABLE 2-continued

| | |
|---|---|
| | S4c[−S4t + C4p · S4t + S4p(C4t + 1)](C2d − 1) + C8c · C4p(3 − 4 · Cd + C2d) − S8c · S4p(3 − 4 · Cd + C2d)}(1/64) |
| $A_7 =$ | {[S4t(3 − 4 · Cd + C2d) + (C4p · S4t + S4p · C4t)(3 + 4 · Cd + C2d)] + C4c[−S4t − C4p · S4t − S4p · (C4t − 1)](C2d − 1) + S4c[(C4t + 1) − C4p · (C4t − 1) + S4p · S4t](C2d − 1) − C8c · S4p(3 − 4 · Cd + C2d) − S8c · C4p(3 − 4 · Cd + C2d)}(1/64) |
| $A_8 =$ | {C2c[−(4 · S2t · Sd) + (C4p · S2t + S4p · C2t)(2 · Sd + S2d)] + S2c[(2 · C2t · S2d) + (C4p · C2t − S4p · S2t)(2 · Sd + S2d)] + C6c[C4p · S2t + S4p · C2t](2 · Sd − S2d) + S6c[C4p · C2t − S4p · S2t](2 · Sd − S2d)}(1/32) |
| $A_9 =$ | [(C2p · S2t + S2p · C2t)(Cd + 1) + C4c(C2p · S2t + S2p · C2t)(Cd − 1) + S4c(C2p · C2t − S2p · S2t)(Cd − 1)](⅛) |
| $A_{10} =$ | {[−S4t(3 − 4 · Cd + C2d) + (C4p · S4t + S4p · C4t)(3 + 4 · Cd + C2d)] + C4c[−S4t + C4p · S4t + S4p(C4t − 1)](C2d − 1) + S4c[(C4t + 1) + C4p(C4t − 1) − S4pS4t](C2d − 1) − C8c · C4p(3 − 4 · Cd + C2d) − S8c · C4p(3 − 4 · Cd + C2d)}(1/64) |
| $A_{11} =$ | {[(3 + 4 · Cd + C2d) + C4t(3 − 4 · Cd + C2d) + (C4p · C4t + S4p · S4t)(3 + 4 · Cd + C2d)] + C4c[(C4t + 1) − C4p(C4t + 1) + S4p · S4t](C2d − 1) + S4c[S4t + C4p · S4t + S4p(C4t + 1)](C2d − 1) − C8c · C4p(3 − 4 · Cd + C2d) + S8c · S4p(3 − 4 · Cd + C2d)}(1/64) |
| $A_{12} =$ | {C2c[(2 · C2t · S2d) + (−C4p · C2t + S4p · S2t)(2 · Sd + S2d)] + S2c[(4 · S2t · Sd) + (C4p · S2t + S4p · C2t)(2 · Sd + S2d)] + C6c[C4p · C2t − S4p · S2t](2 · Sd − S2d) + S6c[−C4p · S2t − S4p · C2t](2 · Sd − S2d)}(1/32) |
| $A_{13} =$ | [C2c(−C2p · S2t − S2p · C2t) + S2c(−C2p · C2t + S2p · S2t)] · Sd(¼) |
| $A_{14} =$ | {C2c[−S4t(2Sd − S2d) − (C4p · S4t + S4p · C4t)(2 · Sd + S2d)] + S2c[−(2 · Sd + S2d) + C4t(2 · Sd − S2d) + (−C4p · C4t + S4p · S4t)(2 · Sd + S2d)] − C6c · S4p(2 · Sd − S2d) − S6c · C4p(2 · Sd − S2d)}(1/32) |
| $A_{15} =$ | {C2c[−(2 · Sd + S2d) + C4t(2 · Sd − S2d) + (C4p · C4t − S4p · S4t)(2 · Sd + S2d)] + S2c[S4t(2 · Sd − S2d) − (C4p · S4t + S4p · C4t)(2 · Sd + S2d)] − C6c · C4p(2 · Sd − S2d) + S6c · S4p(2 · Sd − S2d)}(1/32) |
| $A_{16} =$ | [C2t + C4c(−C4p · C2t + S4p · S2t) + S4c(C4p · S2t + S4p · C2t)](C2d − 1)(1/16) |

In operation, a series of signals $I_{out}$ is collected at different configuration of {p, c, d, t}. Each configuration is set by rotating the polarizer azimuth and/or the retarder azimuth and/or by changing the retarder phase shift "d" and/or changing the chirality "t" of the chiroptics. For each configuration {p, c, d, t}, which has known values of p, c, d, t, and $I_{in}$, equation 7 links the measured signal $I_{out}$ to the sample Mueller matrix and therefore it forms a system of linear equations of the variables $M_k$ and metrology system coefficients $A_k$(p, c,d,t), with one equation per configuration {p, c, d, t}. The number of equations is the number of signal acquisitions $I_{out}$. With the index "y" indicating each configuration {p,c,d,t}, the system of linear equations can be written as:

$$I_y = I_{in} \sum_{k=1}^{16} A_{yk} \cdot M_k \quad \text{eq. 8}$$

By solving this system of linear equations, the Mueller matrix of the sample is obtained. However, in order to obtain all 16 elements of the sample Mueller matrix, at least 16 independent equations are required, which means that the set of configurations {p,c,d,t} needs to be chosen carefully so the matrix $A_{yk}$ has a rank 16 (an example is presented below), where the index "y" identifies each configuration (p,c,d,t) for $A_k$. If the number of equations ($N_E$) is larger than 16 but the rank of $A_{yk}$ remains 16, then the system of equations is over-determined but still can be solved by, for example, minimum least squares or by any other method for over-determined linear equations. The number of equations may be less than 16 or, in some instances may be equal to or larger than 16, but the number of independent equations ($N_{IE}$) may be less than 16. In these last scenarios $N_{IE}$=rank ($A_{yk}$)<16 and equation 8 cannot be solved to get all the $M_k$ elements of the Muller matrix. However, it is still possible to extract from equation 8 $N_{IE}$ independent quantities, with each quantity being a linear combination of some elements of the sample Mueller matrix (an example is presented below), and some of the $N_{IE}$ quantities may still be single Mueller elements. These independent quantities, which include linear combinations of elements, are denoted as $L_l$, where the index "l" ranges from 1 to $N_{IE}$ and the set of $\{L_l\}$ is referred to herein as a "partial Mueller matrix". $L_l$ can be written in a generic form as the product of a sparse matrix $[B_{lk}]$ by the sample Mueller matrix in its vector form $M_k$:

$$L_l = \sum_{k=1}^{16} B_{lk} \cdot M_k \qquad \text{eq. 9}$$

The system of equations 8 becomes then:

$$I_y = I_{in} \sum_{l=1}^{N_{IE}} C_{yl} \cdot L_l \qquad \text{eq. 10}$$

where $[C_{yl}] = [A_{yk}] \cdot [B_{lk}]^T \cdot ([B_{lk}] \cdot [B_{lk}]^T)^{-1}$ The system of equations 10 is solvable for all $L_l$ since per definition, $L_l$ is chosen such that rank ($C_{yl}$)=$N_{IE}$. The partial Mueller matrix $\{L_l\}$ is not unique in the sense that for a given under-determined system of equations 8, where rank ($A_{yk}$) <16, several different sets $\{L_l^{(1)}\}, \{L_l^{(2)}\}, \ldots \{L_l^{(n)}\}$, can be established, each one forming a solvable system of equations 10.

For a given sample, any one of the partial Mueller matrices constitute a group of $N_{IE}$ functions of wavelength λ, one per element $L_l$, and thus are de facto a group of spectra that can be used to characterize the sample and, in particular, can be used in a model-base application to infer the sample structure composition and the sample parameters of interest. Nevertheless, some partial Mueller matrices are more practical than others; the partial Mueller matrices that present a high sensitivity to the sample parameters of interest are preferable. The partial Mueller matrices for which the matrix $[B_{lk}]$ (eq. 9) does not depend on "p", "c", "d" or "t" are also preferable. The reason for this is that "p", "c", "d" and "t" are ultimately tool dependent quantities and each tool might have a slightly different point of operation. If $\{L_l\}$ depends on "p" or "c" or "d" or "t", then for one given sample the spectra of the partial Mueller matrix will be slightly different when measured in different tools, even if the tools are similar. In other words, the spectra of such a partial Mueller matrix will be sample and tool dependent. While this is not a limitation for a model-base applications, it may introduce additional difficulties when attempting to manage tool-to-tool matching in a fleet of tools.

The series of signals $I_{out}$ is collected for different configurations {p, c, d, t}, where at least one component (the chirality "t") is changed. For example, the signals $I_{out}$ may be produced by based on configurations {c,t}, i.e., changeable retarder azimuth "c" and chirality "t", with the other components "p" and "d" are held constant. Other configurations may be produced using one or more of the following: {t}, {p,t}, {d,t}, {p,c,t}, {p,d,t}, {c,d,t}, and {p,c,d,t}.

All these above-described configurations are specific cases of the metrology device 100, shown in FIG. 1. Moreover, the sample 108 can be any sample, with or without cross-polarization and/or de-polarization behaviors. Using the above-described configurations, the sample Mueller matrix or a sample partial Mueller matrix may be acquired and used in a model-base application to infer the sample parameters of interest.

In one specific case, using a {c,t} configuration, the sample Mueller matrix is obtained. The signal $I_y$ is acquired at different configurations of {c,t} and "p" and "d" remain fix. The retarder 116, shown in FIG. 1, can be a continuously rotating or a step rotating retarder or a discrete number of individual retarders oriented at different azimuths "c" mounted on a sliding bar or on a rotating wheel or any other construction that allow to change the retarder azimuth "c" a discrete number of times. Similarly, the chiroptic 118 can be a switchable molecular chiroptic element activated by a an electric field or a number of discrete chiroptic crystals mounted on a sliding bar or on rotating wheel or any other construction that allow to change the chirality "t" a discrete number of times.

In this example the chirality "t" must have at least 3 different values where one of the values is not a multiple of 45 degrees. For each "t", the signal at Nc different positions of "c" is acquired. In other words, the retarder 116 undergoes a cycle for each state of "t", and the cycle is repeated for Nt different values of "t". The total number of signals $I_y$ is thus Nt×Nc and so the number of equations in equation 7 is Nt×Nc. In this example, we assume Nc≧9 so we can reduce the number of equations in equation 7 to Nt×9 by extracting the nine Fourier coefficients along "c" for each chirality state "t". The signals, i.e. the Fourier transforms of $I_y$ along "c", may be written as $I_{y*}=I_h(t)$ where the index "h" stands for the Fourier component "h" as defined in equation 3. By simple rearrangement of equation 7, $I_{y*}$ can be written as:

$$I_{y*} = I_h(t) = I_{in} \sum_{k=1}^{16} A_{hk}(t) \cdot M_k \qquad \text{eq. 11}$$

where $$A_{hk}(t) = \sum_{i=1}^{5} \sum_{j=1}^{5} \sum_{g=1}^{5} U_{hijgk} \cdot \Theta_g \cdot \Phi_j(t) \cdot \Lambda_i$$

This system of equations, one per Fourier component "h" and per chirality "t" has a rank=16 as long as one of the chiralities values is not a multiple of 45 degrees. Since 'p', 'd', 't' and $I_{in}$ are known, this system can be solved to obtain the sample Mueller matrix $M_k$:

$$M_k = ([A_{y*,k}]^T \cdot [A_{y*,k}])^{-1} \cdot [A_{y*,k}]^T [I_{y*}]/I_{in} \qquad \text{eq. 12}$$

where $$A_{y*,k} \equiv A_{hk}(t)$$

Figure 4:
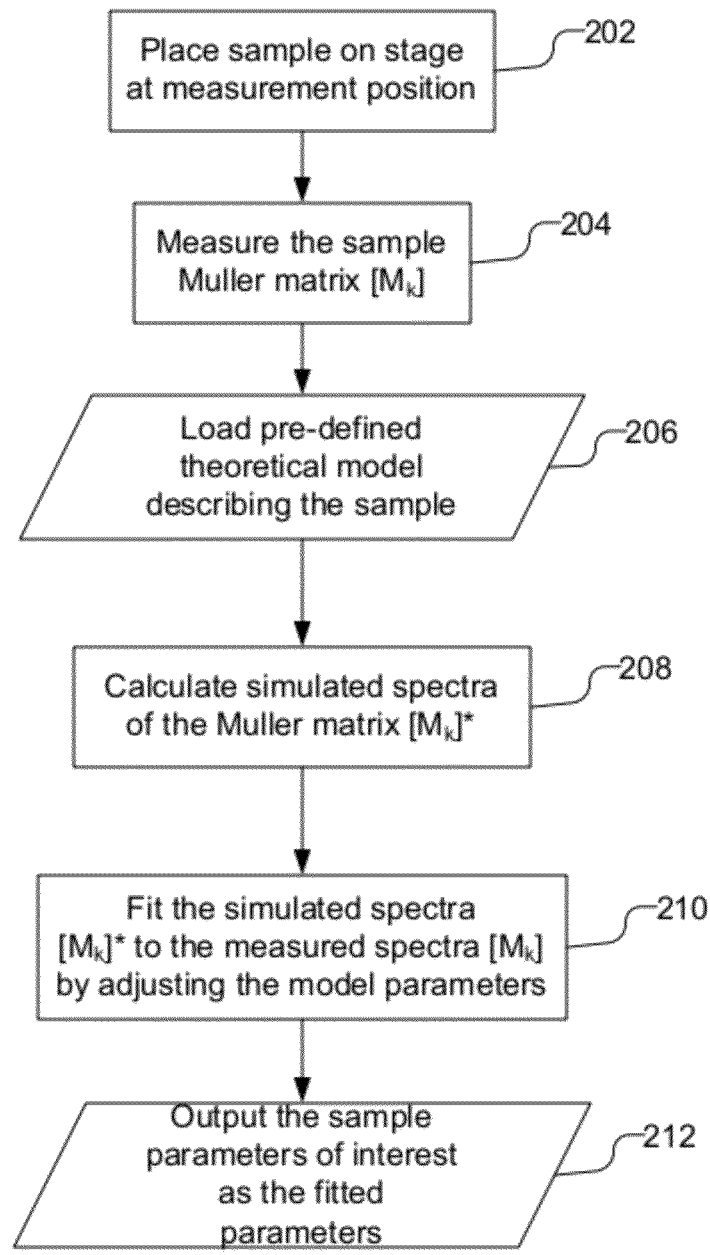
FIG. 4 illustrates the process of measurement of a sample structural parameter of interest using a sample Mueller matrix spectra.

FIG. 4 illustrates the process of measurement of a sample structural parameter of interest using the sample Mueller matrix $[M_k]$. As illustrated, the sample 108 is placed on the stage 112 at the measurement position, i.e., under the optics 118, (202). The spectra for the sample Muller matrix $[M_k]$ is measured, as described in the flow chart illustrated in FIG. 5 below (204). A pre-defined theoretical model describing the sample is loaded (206) and simulated spectra for the Mueller matrix $[M_k]$* is calculated for the theoretical model, which may be performed before or after the sample is loaded and the Mueller matrix [$M_k$] measured. For example, the calculation of simulated spectra for the Mueller matrix [$M_k$]* for the model may be performed in real time or may be pre-calculated and stored in a library, along with simulated spectra for the Mueller matrix [$M_k$]* for models having varying parameters. The simulated spectra for the Mueller matrix [$M_k$]* for the model is fit to the measured spectra for the sample Mueller matrix [$M_k$] by adjusting the model parameters (210). Once an acceptable fit of the simulated and measured spectra of the model Mueller matrix [$M_k$]* and the sample Mueller matrix [$M_k$] is achieved, the sample parameters of interest are output as the fitted parameters (212), which may be stored in memory 134, displayed, or otherwise reported.

Figure 5:
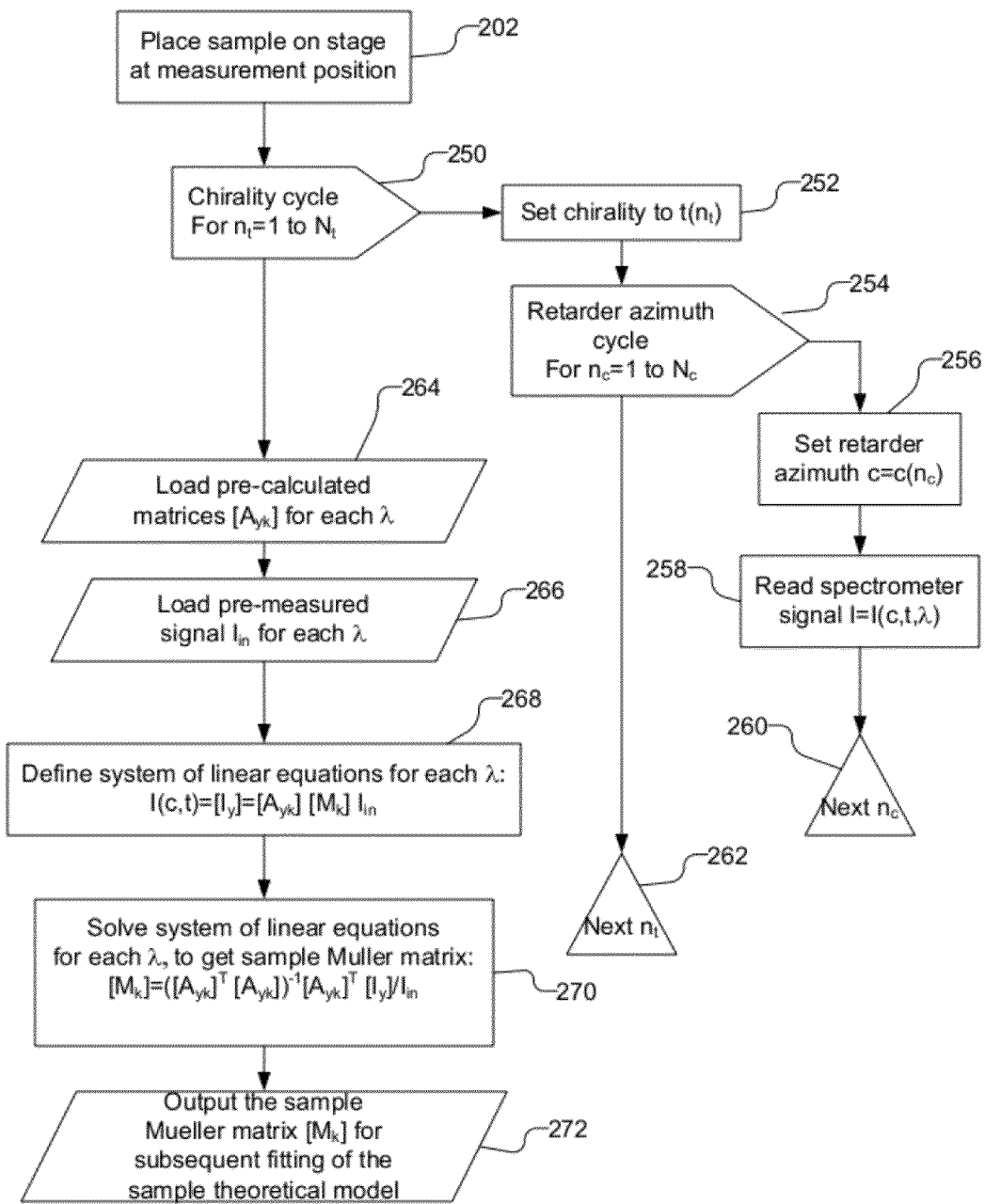
FIG. 5 illustrates the process of measuring the spectra for the sample Muller matrix for a metrology device with a variable chiroptic and retarder.

FIG. 5 illustrates measuring the sample Muller matrix [$M_k$] (step 204, above) for a metrology device 100 with a {c,t} configuration. As illustrated, after the sample 108 is placed on the stage 112 at the measurement position (202), a retarder azimuth cycle (252) from $n_c=N_c$ is performed within a chirality cycle from $n_t=N_t$ (250). Thus, with the chirality set to $t(n_t)$ (252), the retarder azimuth cycle (254) is performed by setting the retarder azimuth $c=c(n_c)$ (256) and reading the spectrometer 120 signal $I=I(c,t,\lambda)$ (258), and the retarder azimuth value is increased to the next (260) until the retarder azimuth cycle is complete (254). The chirality value is increased to the next $n_t$ (262) and the retarder azimuth cycle (254) is repeated until the chirality cycle is complete (250). Thus, spectrometer 120 signals for all values of c, t, and $\lambda$ are obtained. It should be understood that the polarizer axis azimuth p, and retardation between fast and slow axis d may be similarly treated in addition to or in place of the retarder azimuth c.

The pre-calculated matrices [$A_{yk}$] for each X is loaded (264) and the pre-measured signal $I_{in}$ for each $\lambda$ is loaded (266). The system of linear equations for each $\lambda$ is defined as described above in equation 8 (268). The system of linear equations for each $\lambda$ may then be solved to obtain the Mueller matrix [$M_k$] for the sample (270), as described above in equation 12. The sample Mueller matrix [$M_k$] is output and stored, e.g., in memory 134, to be subsequently fit with the sample theoretical model (272).

Figure 6:
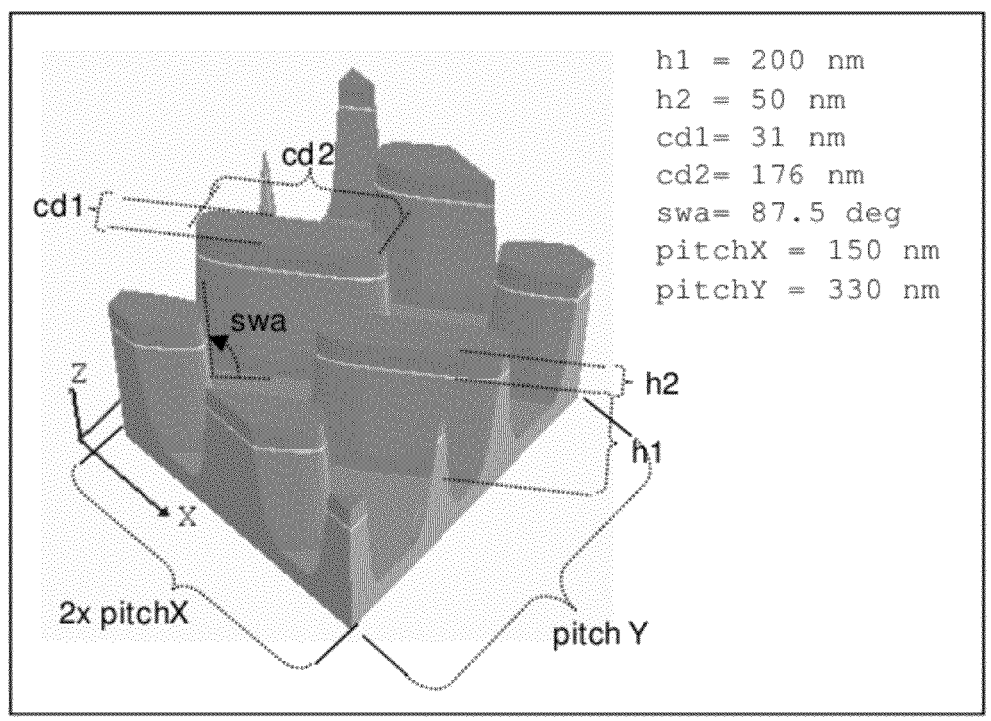
FIG. 6 illustrates a shallow trench isolation (STI) target along with the fitted parameters of interest.
Figure 7:
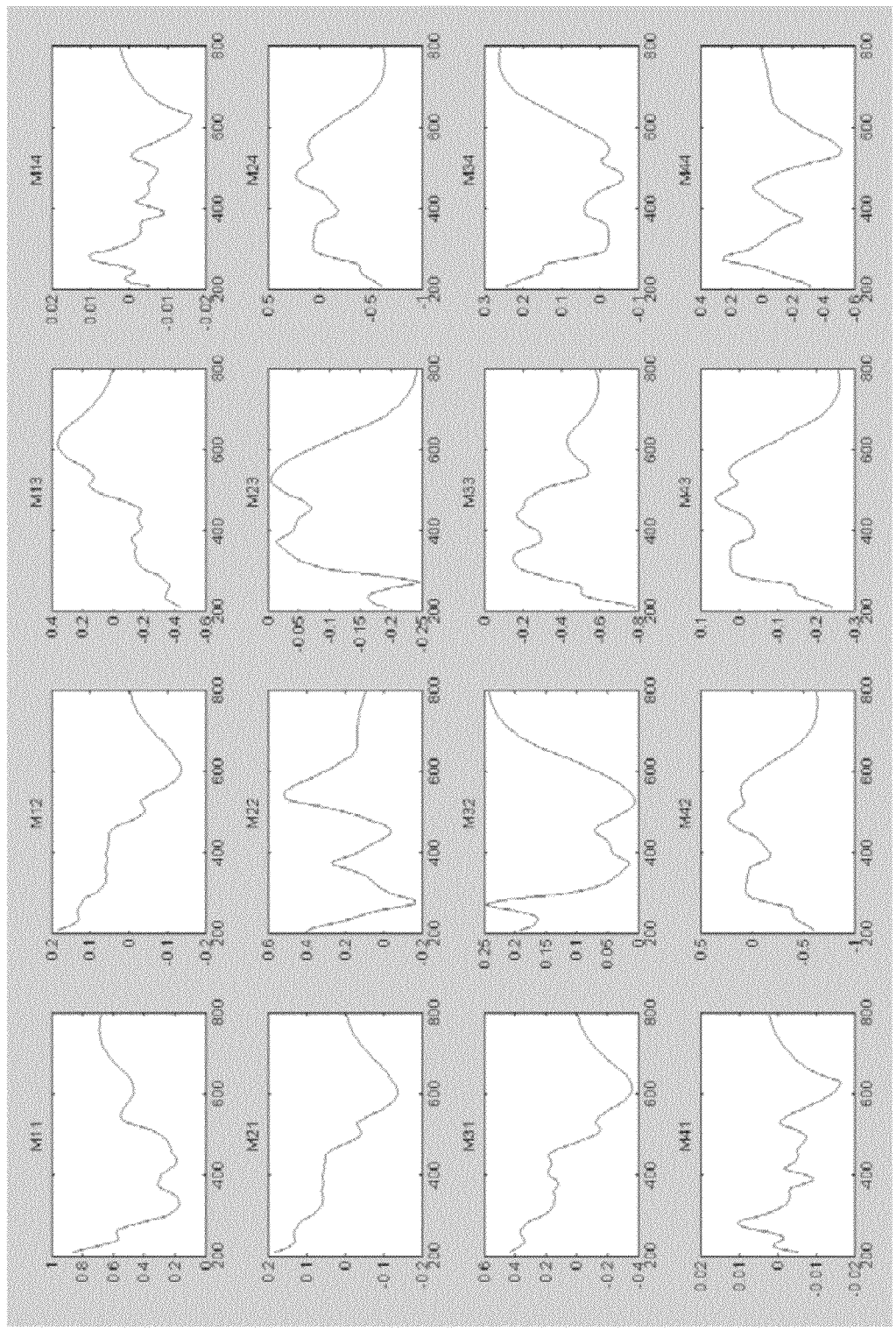
FIG. 7 illustrates the simulated spectra for the Mueller matrices for the target of FIG. 6.

FIG. 6 illustrates a shallow trench isolation (STI) target that may be measured using the above-described process, along with the fitted parameters of interest. In general, targets are becoming more and more complex due to the increasingly complexity of the IC manufacturing processes. The targets are often 3D complex structures, such as that illustrated in FIG. 6, which present naturally strong cross-polarization effects. Such effects are strongly sensitive to the target structure geometry. By using Mueller matrix spectra instead of traditional Ellipsometry spectra or Polarized-Reflectometry spectra in a model-base approach application, a higher sensitivity of the parameters of interest may be obtained. Moreover, the parameters of interest present a lower correlation during the fitting process. As a result the inferred parameters of interest present in general a higher accuracy and better precision if the noise levels of all spectra are comparable. Additionally, Mueller matrix allows fitting some type of parameters that present null sensitivity on traditional Ellipsometry and polarized-Reflectometry (e.g., side wall angle of an asymmetric grating or overlay of a symmetric double-patterning structure). FIG. 7 illustrates the simulated spectra for the Mueller matrices, produced as described above.

It should be understood that it is not necessary to acquire data at evenly spaced azimuths "c", nor is it necessary to measure at the same azimuths "c" for each chirality "t", i.e., synchronism between "t" and "c" need not be imposed. Thus, the number of $N_E$ signals may be acquired at arbitrary known values of "c" and "t", as long $N_E>=16$ and the system of equation 7 present a rank=16.

In another example, using a configuration {t}, a sample partial Mueller matrix is obtained. The signal $I_y$ is obtained at different at different values of "t" and "p", "c" and "d" remain fix. Furthermore, the values of "c" and "d" can be zero which means that the retarder element 116 shown in FIG. 1 can be absent from the system. The chiroptic 118 can be a switchable molecular chiroptic element activated by a an electric filed or a number of discrete chiroptic crystals mounted on a sliding bar or on rotating wheel or any other construction that allow to rotate the electromagnetic field of the beam by "t" degrees, a discrete number of times Nt. In this example the chirality "t" has at least 5 different values. The signal $I_y$ is acquired at $N_t>=5$ values of "t". Therefore, as in the previous example, we can reduce the number of equations in equation 7 to only 5 by extracting the Fourier coefficients along "t", $I_j$, where the index "j" goes from 1 to 5. By simple rearrangement of equation 7, $I_j$ can be written as:

$$I_j = I_{in} \sum_{k=1}^{16} A_{jk}(t) \cdot M_k \qquad \text{eq. 13}$$

where $$A_{jk}(t) = \sum_{h=1}^{9} \sum_{i=1}^{5} \sum_{g=1}^{5} U_{hijgk} \cdot \Theta_g \cdot \Lambda_i \cdot \Omega_h$$

A full development of the equations (11) is given below where, once again, we have used a short notation $\cos(nx) = Cnx$ and $\sin(nx) = Snx$, n being an integer and x the variable.

$$I_1 = [M_{33}+M_{22}+2 \cdot M_{11}] \cdot I_{in}/8$$

$$I_2 = [C2p \cdot (M_{21}+M_{12})+S2p \cdot (M_{31}+M_{13})] \cdot I_{in}/4$$

$$I_3 = [-S2p \cdot (M_{21}+M_{12})+C2p \cdot (M_{31}+M_{13})] \cdot I_{in}/4$$

$$I_4 = [C4p \cdot (M_{22}-M_{33})+S4p \cdot (M_{32}+M_{23})] \cdot I_{in}/8$$

$$I_5 = [-S4p \cdot (M_{22}-M_{33})+C4p \cdot (M_{32}+M_{23})] \cdot I_{in}/8 \qquad \text{eq. 14}$$

An inspection of equation 14 shows that only a partial Mueller matrix of 5 elements can be extracted. One case of practical interest would be:

$$\{L_l\} = \{L_1 = M_{21}+M_{12}$$

$$L_2 = M_{31}+M_{13}$$

$$L_3 = M_{23}+M_{32}$$

$$L_4 = M_{11}+M_{22}$$

$$L_5 = M_{11}+M_{33} \qquad \text{eq. 15}$$

All the elements $L_l$ depends only on the sample Mueller matrix and therefore makes it particularly suitable for model-base applications. To solve equation 14 to get the partial Mueller Matrix equation 15, the matrix [$B_{lk}$] can be defined as per equation 9:

$$[B_{lk}] = \frac{1}{2} \cdot \begin{bmatrix} 0 & 1 & 0 & 0 & 1 & 0 & 0 & 0 & 0 & 0 & 0 & 0 & 0 & 0 & 0 \\ 0 & 0 & 1 & 0 & 0 & 0 & 0 & 1 & 0 & 0 & 0 & 0 & 0 & 0 & 0 \\ 0 & 0 & 0 & 0 & 0 & 1 & 0 & 0 & 1 & 0 & 0 & 0 & 0 & 0 & 0 \\ 1 & 0 & 0 & 0 & 0 & 1 & 0 & 0 & 0 & 0 & 0 & 0 & 0 & 0 & 0 \\ 1 & 0 & 0 & 0 & 0 & 0 & 0 & 0 & 0 & 1 & 0 & 0 & 0 & 0 & 0 \end{bmatrix} \quad \text{eq. 16}$$

The system of equations 14 can then be solved as:

$$[L_l] = ([C_{yl}]^T \cdot [C_{yl}])^{-1} \cdot [C_{yl}]^T \cdot [I_l]/I_{in}$$

where $$[C_{yl}] = [A_{yk}] \cdot [B_{lk}]^T \cdot ([B_{lk}] \cdot [B_{lk}]^T)^{-1} \quad \text{eq. 17}$$

Figure 8:
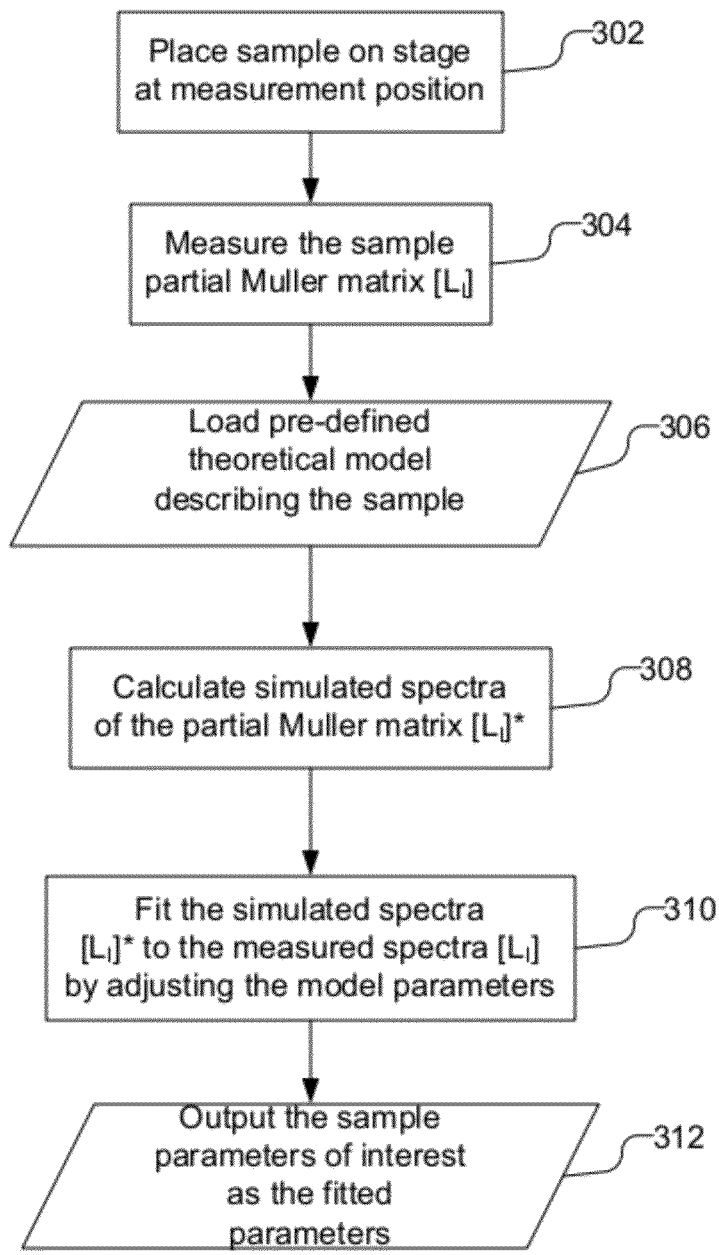
FIG. 8 illustrates the process of measurement of a sample structural parameter of interest using spectra for a partial Mueller matrix for a sample.

FIG. 8 illustrates the process of measurement of a sample structural parameter of interest using a partial Mueller matrix $[L_l]$. Similar to the flow chart described in FIG. 4, the sample 108 is placed on the stage 112 at the measurement position, i.e., under the optics 118, (302). The spectra for the partial sample Mueller matrix $[L_l]$ is measured, as described in the flow chart illustrated in FIG. 9 below (304). A pre-defined theoretical model describing the sample is loaded (306) and simulated spectra for the Mueller matrix $[L_l]$* is calculated from the theoretical model, which may be performed before or after the sample is loaded and the Mueller matrix $[L_l]$ measured. For example, the calculation of simulated spectra for the Mueller matrix $[L_l]$* for the model may be performed in real time or may be pre-calculated and stored in a library, along with simulated spectra for the Mueller matrix $[L_l]$* for models having varying parameters. The simulated spectra for the Mueller matrix $[L_l]$* for the model is fit to the measured spectra for the sample Mueller matrix $[L_l]$ by adjusting the model parameters (310). Once an acceptable fit of the simulated and measured spectra of the model Mueller matrix $[L_l]$* and the sample Mueller matrix $[L_l]$ is achieved, the sample parameters of interest are output as the fitted parameters (312), which may be stored in memory 134, displayed, or otherwise reported.

Figure 9:
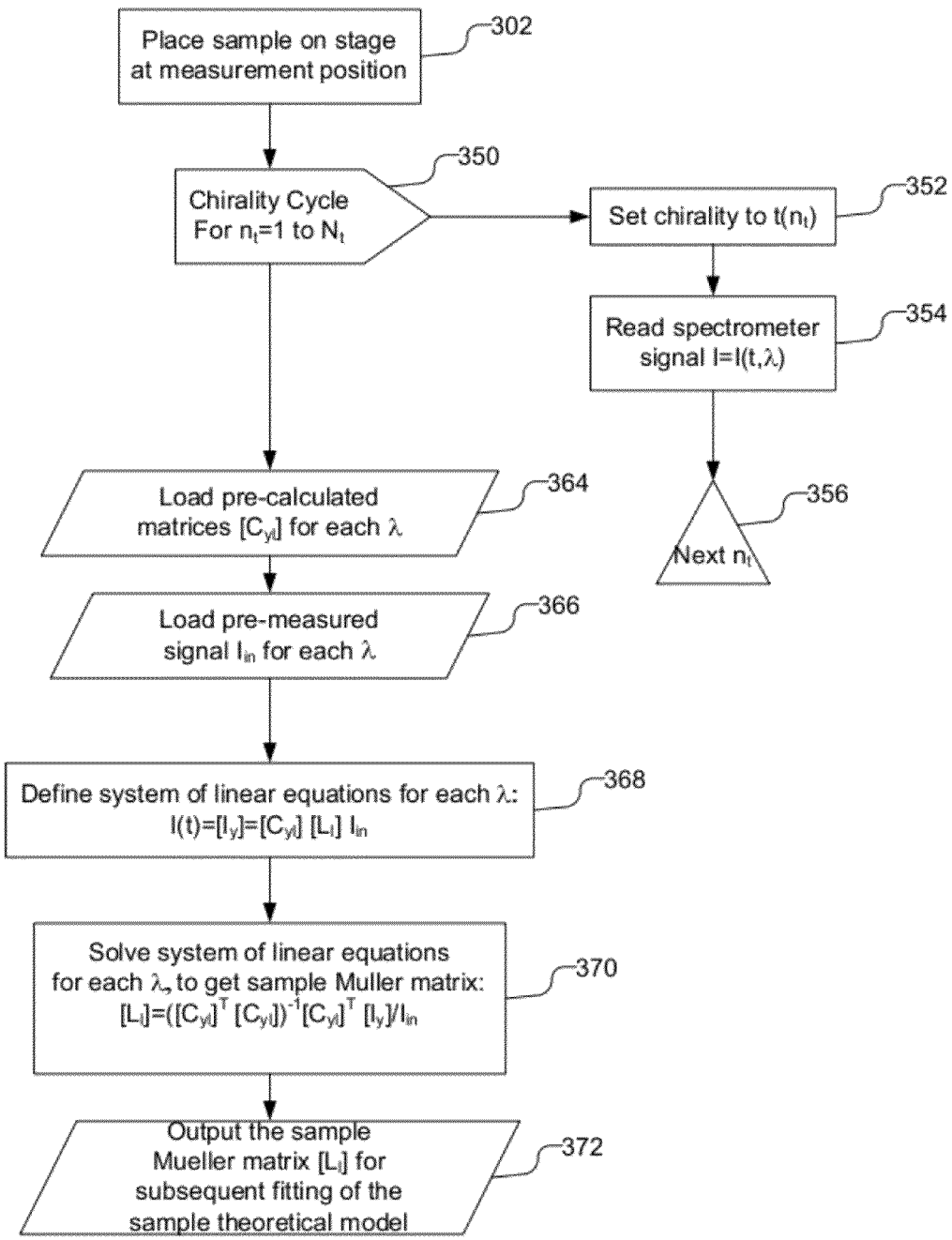
FIG. 9 illustrates the process of measuring the spectra for a partial Muller matrix for a metrology device with a variable chiroptic.

FIG. 9 illustrates measuring the partial sample Muller matrix $[L_l]$ (step 304, above) for a metrology device 100 with a {t} configuration. As illustrated, after the sample 108 is placed on the stage 112 at the measurement position (302), a chirality cycle from $n_t=1$ to $N_t$ is performed (350), where the chirality is set to $t(n_t)$ (352), the spectrometer 120 signal $I=I(t,\lambda)$ is read (354), and the chirality value is increased to the next $n_t$ (356) and the process repeated until the chirality cycle is complete (350). Thus, spectrometer 120 signals for all values of t and $\lambda$ are obtained.

The pre-calculated matrices $[C_{yl}]$ for each $\lambda$ is loaded (364) and the pre-measured signal $I_{in}$ for each $\lambda$ is loaded (366). The system of linear equations for each $\lambda$ is defined as described above in equation 10 (368). The system of linear equations for each $\lambda$ may then be solved to obtain the Mueller matrix $[L_l]$ for the sample (370), as described above in equation 17. The sample Mueller matrix $[L_l]$ is output and stored, e.g., in memory 134, to be subsequently fit with the sample theoretical model (372).

Figure 10:
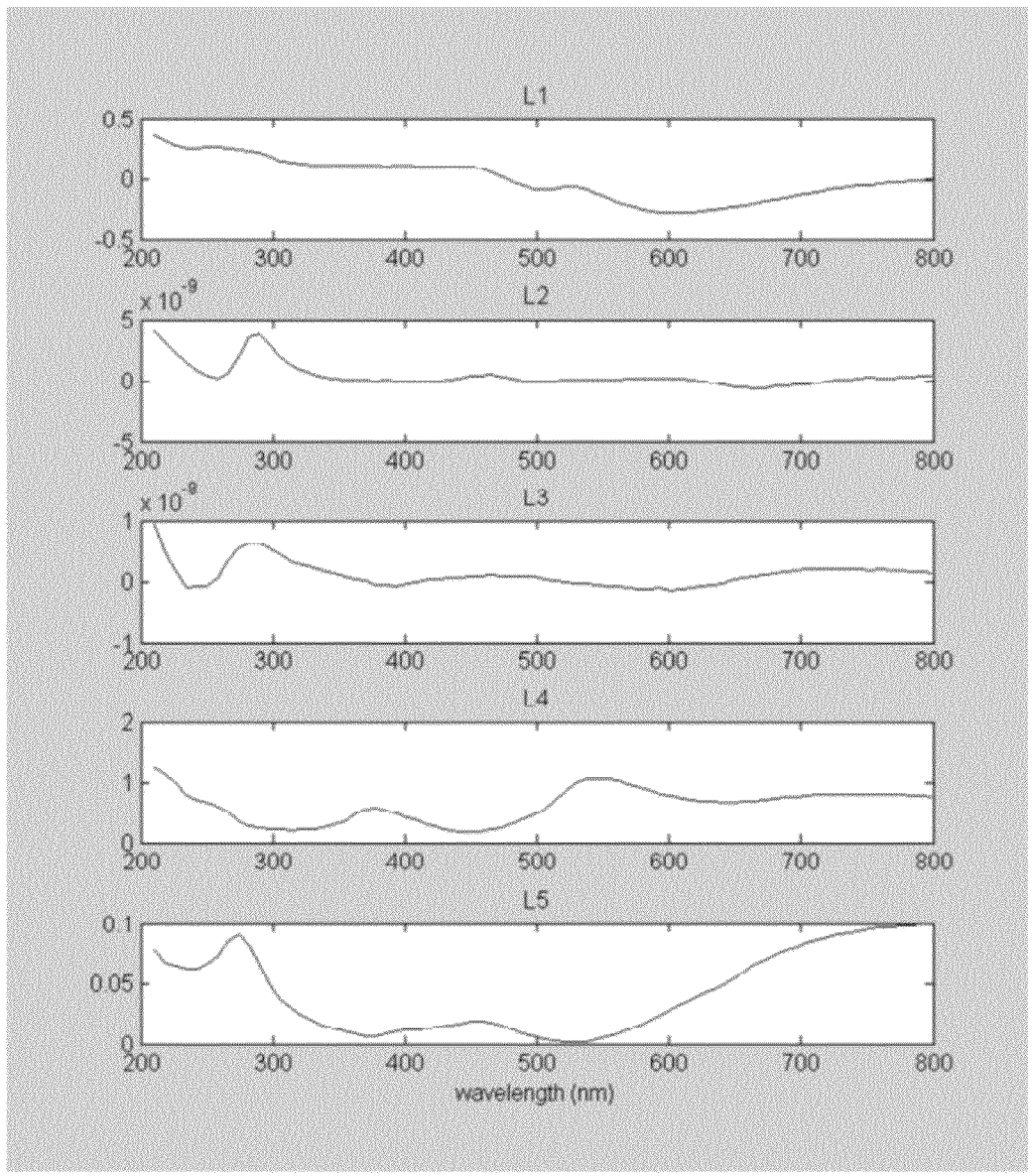
FIG. 10 illustrates the simulated spectra for the partial Mueller matrix produced for the STI sample shown in FIG. 6.

FIG. 10 illustrates the simulated spectra for the partial Mueller matrix produced for the STI sample shown in FIG. 6 using the above-described process.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method comprising:
   producing a broadband beam of light that is incident on and reflected by a sample;
   introducing multiple variations in a state of polarization of the beam of light using a chiroptic;
   detecting light reflected from the sample with the variations in the state of polarization of the beam of light induced by the chiroptic and the sample;
   determining at least a partial Muller matrix using the detected light with the variations in the state of polarization of the beam of light induced by the chiroptic and the sample;
   using the at least partial Muller matrix to determine a characteristic of the sample; and
   reporting the characteristic of the sample by at least one of storing in memory and displaying.

2. The method of claim 1, further comprising introducing multiple variations in at least one of polarization azimuth and phase retardation of the beam of light.

3. The method of claim 1, wherein determining at least a partial Muller matrix comprises measuring spectra for the at least partial Muller matrix for the sample, and wherein using the at least partial Muller matrix to determine a characteristic of the sample comprises fitting simulated spectra for an at least partial Mueller matrix for a model to the measured spectra for the at least partial Mueller matrix for the sample by adjusting model parameters.

4. The method of claim 3, wherein the simulated spectra for the at least partial Mueller matrix for the model is stored in a library.

5. The method of claim 1, wherein determining at least a partial Muller matrix comprises:
   defining a system of linear equations for a plurality of wavelengths $\lambda$ of the broadband beam of light using an intensity $I_{in}$ of the produced broadband beam of light, an intensity signal $I_y$ of the detected light for each configuration (y) of chirality of the chiroptic, and pre-calculated metrology device coefficients; and
   solving the system of linear equations to determine the at least a partial Muller matrix.

6. A metrology device comprising:
   a broadband light source that produces a beam of light to be incident on a sample along a light path;
   a spectrometer to receive reflected light from the sample along the light path;
   a chiroptical element that is located in the light path before the spectrometer, the chiroptical element is variable to produce a plurality of known chiralities; and
   a processor coupled to the spectrometer and the chiroptical element and including a computer operable medium, wherein the computer operable medium includes instructions that cause the processor to control the state of the chiroptical element and to use output signals received from the spectrometer for different known chiralities to determine at least a partial sample Muller matrix and to use the at least a partial sample Muller matrix to determine a characteristic of the sample.

7. The metrology device of claim 6, wherein the beam of light is normally incident on the sample, the metrology device further comprising a beam splitter in the light path between the broadband light source, wherein the chiroptical element is located between the beam splitter and the sample.

8. The metrology device of claim 7, wherein the polarizing element is located between the beam splitter and the sample.

9. The metrology device of claim 7, wherein the polarizing element is located between the broadband light source and the beam splitter, the metrology device further comprising an analyzer element located in the light path between the beam splitter and the spectrometer.

10. The metrology device of claim 6, wherein the beam of light is obliquely incident on the sample, the metrology device further comprising an analyzer element located in the light path between the sample and the spectrometer.

11. The metrology device of claim 10, wherein the chiroptical element is located between the broadband light source and the sample.

12. The metrology device of claim 10, wherein the chiroptical element is located between the sample and the spectrometer.

13. The metrology device of claim 6, further comprising a polarizing element located in the light path between the broadband light source and the sample, the beam of light passing through the polarizing element to produce polarized light, the polarizing element is variable to produce a plurality of known polarization azimuths, the polarized light passing through the chiroptical element, wherein the computer operable medium includes instructions that cause the processor to control the position of the polarizing element and to use output signals received from the spectrometer for different known polarization azimuths, along with the chiralities to determine the at least a partial sample Muller matrix.

14. The metrology device of claim 6, further comprising a retarder element located in the light path between the polarizing element and the spectrometer and that is separate from the retarder element, the polarized light passing through the retarder element, the retarder element is variable to produce a plurality of known retarder azimuths, wherein the computer operable medium includes instructions that cause the processor to control the position of the retarder element and to use output signals received from the spectrometer for different known retarder azimuths, along with the chiralities to determine the at least a partial sample Muller matrix.

15. The metrology device of claim 6, wherein the computer operable medium includes instructions that cause the processor to determine the at least partial sample Muller matrix as measured spectra for the at least partial sample Mueller matrix for the sample, and to fit simulated spectra for an at least partial Mueller matrix for a model to the measured spectra for the at least partial sample Mueller matrix for the sample to determine the characteristic of the sample.

* * * * *